(12) United States Patent
Takada et al.

(10) Patent No.: US 9,795,774 B2
(45) Date of Patent: Oct. 24, 2017

(54) MICRONEEDLE ASSEMBLY FORMULATION FOR SKIN TREATMENT

(75) Inventors: Kanji Takada, Kyoto (JP); Ichiro Ono, Hokkaido (JP)

(73) Assignees: BIOSERENTACH CO., LTD., Kyoto (JP); LABO JUVERSA CO., LTD., Hokkaido (JP)

( * ) Notice: Subject to any disclaimer, the term of this patent is extended or adjusted under 35 U.S.C. 154(b) by 439 days.

(21) Appl. No.: 13/696,621

(22) PCT Filed: Jun. 28, 2012

(86) PCT No.: PCT/JP2012/066546
§ 371 (c)(1),
(2), (4) Date: Nov. 20, 2012

(87) PCT Pub. No.: WO2013/002331
PCT Pub. Date: Jan. 3, 2013

(65) Prior Publication Data
US 2013/0072902 A1 Mar. 21, 2013

(30) Foreign Application Priority Data
Jun. 28, 2011 (JP) .................................. 2011-143371

(51) Int. Cl.
*A61M 37/00* (2006.01)
*A61K 9/70* (2006.01)
(Continued)

(52) U.S. Cl.
CPC ....... *A61M 37/0015* (2013.01); *A61K 9/0021* (2013.01); *A61K 9/70* (2013.01);
(Continued)

(58) Field of Classification Search
CPC .. A61K 9/0021; A61K 9/703; A61K 2800/91; A61M 37/0015;
(Continued)

(56) References Cited

U.S. PATENT DOCUMENTS 8,491,534 B2 * 7/2013 Takada .......................... 604/173
2008/0262444 A1 10/2008 Takada
(Continued)

FOREIGN PATENT DOCUMENTS

EP 2 263 683 12/2010
EP 2 283 809 2/2011
(Continued)

OTHER PUBLICATIONS

The American Heritage Dictionary definition of "Dermal". Definition, available online Jan. 26, 2016 at https://www.ahdictionary.com/word/search.html?q=dermal.*
(Continued)

*Primary Examiner* — Kevin C Sirmons
*Assistant Examiner* — Amber Stiles
(74) *Attorney, Agent, or Firm* — Wenderoth, Lind & Ponack, L.L.P.

(57) ABSTRACT

A problem to be solved of the present invention is to provide a drug formulation and a method of administering an active ingredient which allow the active ingredient to be delivered evenly into the site of action in the skin with high efficiency while ensuring stability of the active ingredient over a long time, and which are easily handled and are less stressful for patients. Mean for solving the problem is a microneedle assembly formulation for skin treatment comprising a platform and a plurality of conical or pyramidal microneedles formed on the platform containing a base composed of a bio-soluble and thread-forming polymer substance and an objective substance retained in the base, wherein the objective substance is a substance effective for prevention or treatment of skin senescence, or treatment of skin scar.

11 Claims, 18 Drawing Sheets

(51) Int. Cl.
*A61K 45/06* (2006.01)
*A61K 9/00* (2006.01)
*A61K 38/18* (2006.01)

(52) U.S. Cl.
CPC .......... *A61K 45/06* (2013.01); *A61K 38/1825* (2013.01); *A61M 2037/0046* (2013.01)

(58) Field of Classification Search
CPC .. A61M 2037/0023; A61M 2037/0046; A61M 2037/0053; A61M 2037/0061
See application file for complete search history.

(56) References Cited

U.S. PATENT DOCUMENTS

| | | | |
|---|---|---|---|
| 2008/0269685 A1* | 10/2008 | Singh | A61K 9/0021 604/173 |
| 2009/0035446 A1* | 2/2009 | Kwon | A61K 9/0021 427/2.1 |
| 2009/0093775 A1* | 4/2009 | Raju et al. | 604/272 |
| 2010/0256594 A1* | 10/2010 | Kimmell | A61M 37/0015 604/506 |
| 2011/0028699 A1* | 2/2011 | Ono | A61K 8/66 530/399 |
| 2011/0028905 A1* | 2/2011 | Takada | A61K 9/0021 604/180 |
| 2011/0152792 A1* | 6/2011 | Takada | A61M 37/0015 604/272 |
| 2011/0276027 A1* | 11/2011 | Trautman et al. | 604/506 |
| 2012/0130306 A1* | 5/2012 | Terahara | A61K 9/0021 604/46 |

FOREIGN PATENT DOCUMENTS

| | | |
|---|---|---|
| JP | 2002-249498 | 9/2002 |
| JP | 2003-342194 | 12/2003 |
| JP | 2005-154321 | 6/2005 |
| JP | 2011-012050 | 1/2011 |
| WO | 2006/080508 | 8/2006 |
| WO | 2009/066763 | 5/2009 |
| WO | 2009/119073 | 10/2009 |
| WO | 2010/140401 | 12/2010 |

OTHER PUBLICATIONS

Sandby-Moller, et al. Investigative Report: Epidermal ZThickness at Different Body Sites: Relationship to Age, Gender, Pigmentation, Blood Content, Skin Type and Smoking Habits, Acta Derm Venereol 2003; 83: 410-413.*
International Preliminary Report on Patentability and Written Opinion dated Aug. 7, 2012 in International (PCT) Application No. PCT/JP2012/066546.
International Search Report dated Aug. 7, 2012 in International (PCT) Application No. PCT/JP2012/066546.
Drug Delivery System, vol. 26, No. 3, May 28, 2011, p. 322 (P07).
Jpn J. Clin. Pharmacol. Ther., vol. 42, No. Suppl, Oct. 31, 2011, p. 290 (1-P-83).
Extended European Search Report dated Oct. 2, 2015 in corresponding European Application No. 12783484.4.
Ito et al., "Self-dissolving microneedles for the percutaneous absorption of EPO in mice", Journal of Drug Targeting, vol. 14 (5) Jun. 1, 2006, pp. 255-261.
Steiling el al., "Fibroblast growth factors: key players in epithelial morphogenesis, repair and cytoprotection", Current Opinion in Biotechnology, vol. 14, No. 5, Oct. 1, 2003, pp. 533-537.
Communication pursuant to Article 94(3) EPC dated Mar. 30, 2017 in corresponding European Application No. 12 783 484.4.

* cited by examiner

[Figure 1]
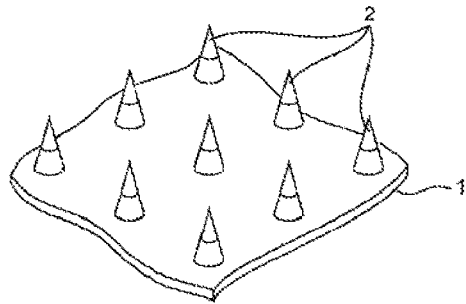
[Figure 2]
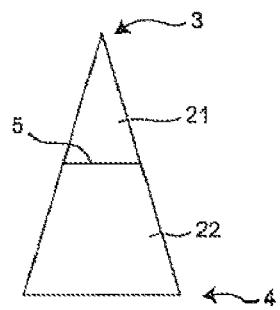
[Figure 3]
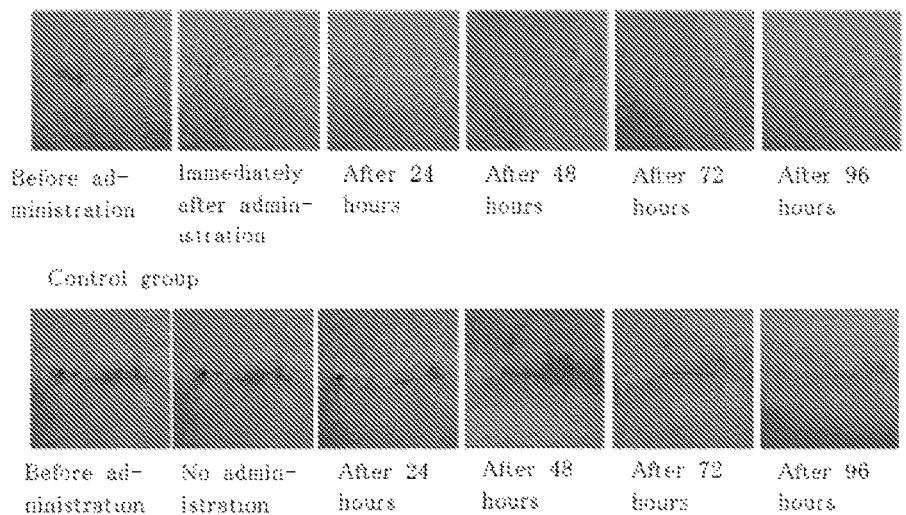

[Figure 4]
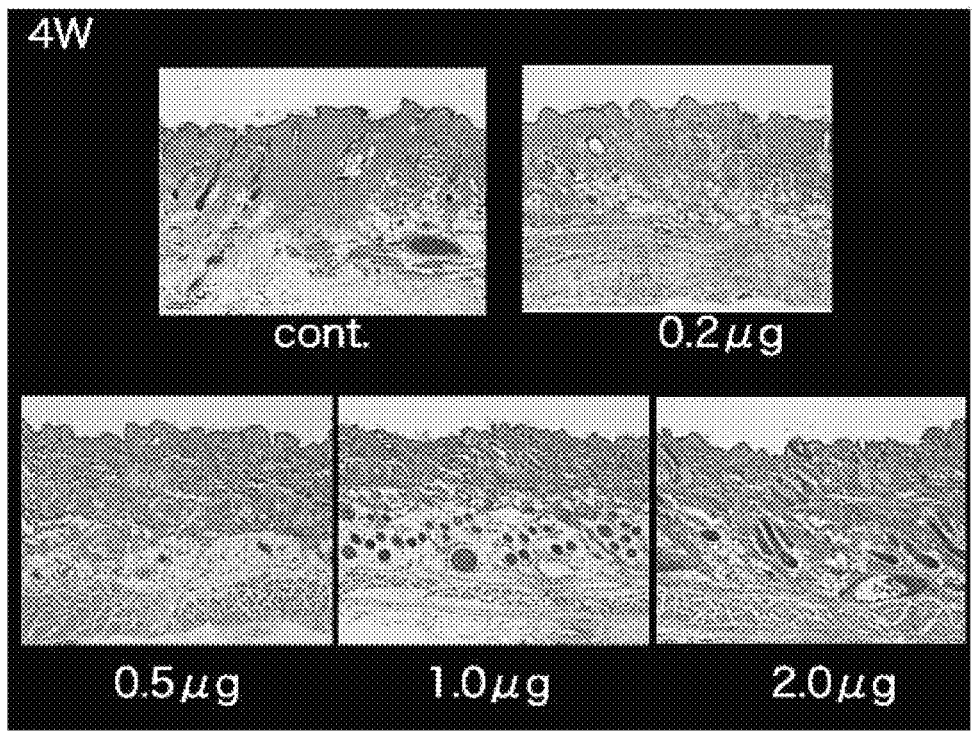
(a)
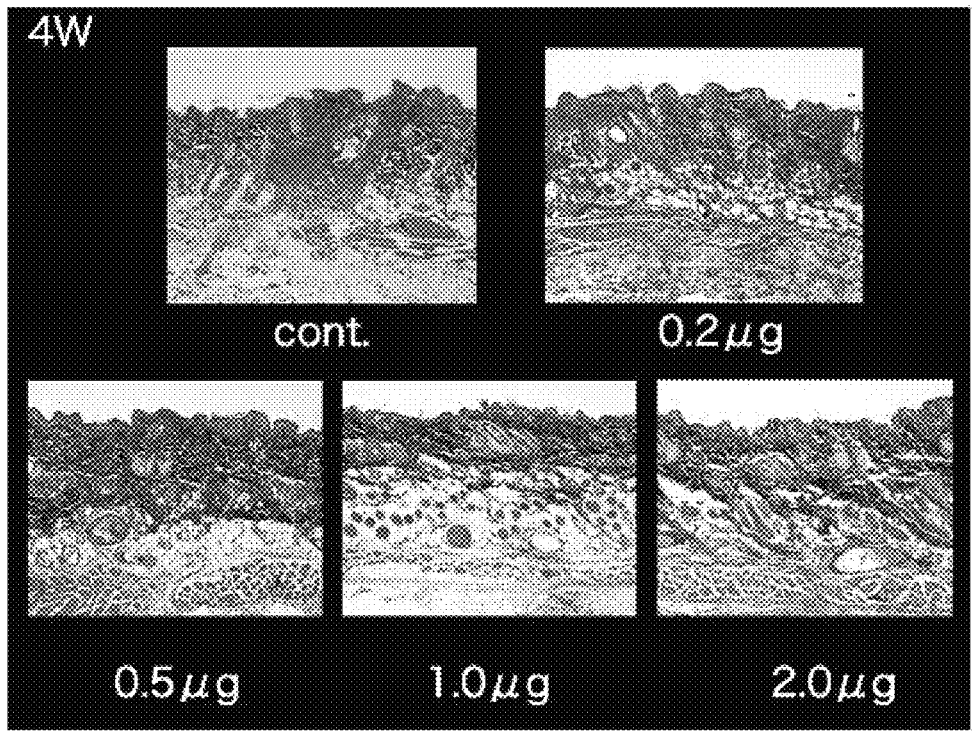
(b)

[Figure 5]
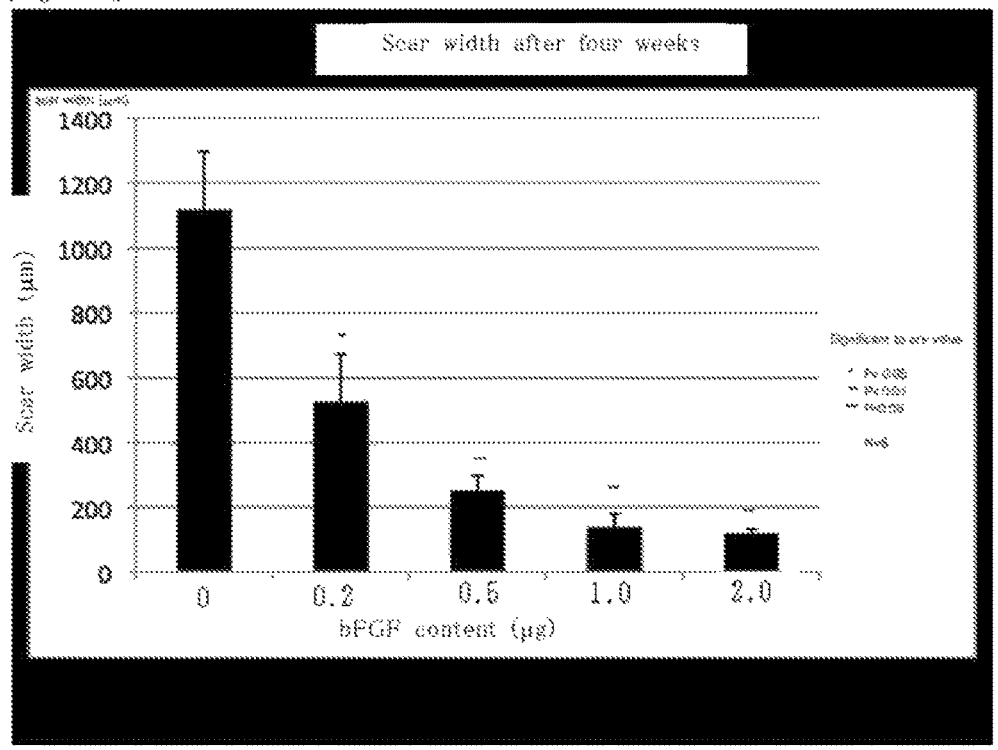
[Figure 6A]

[Figure 6B]
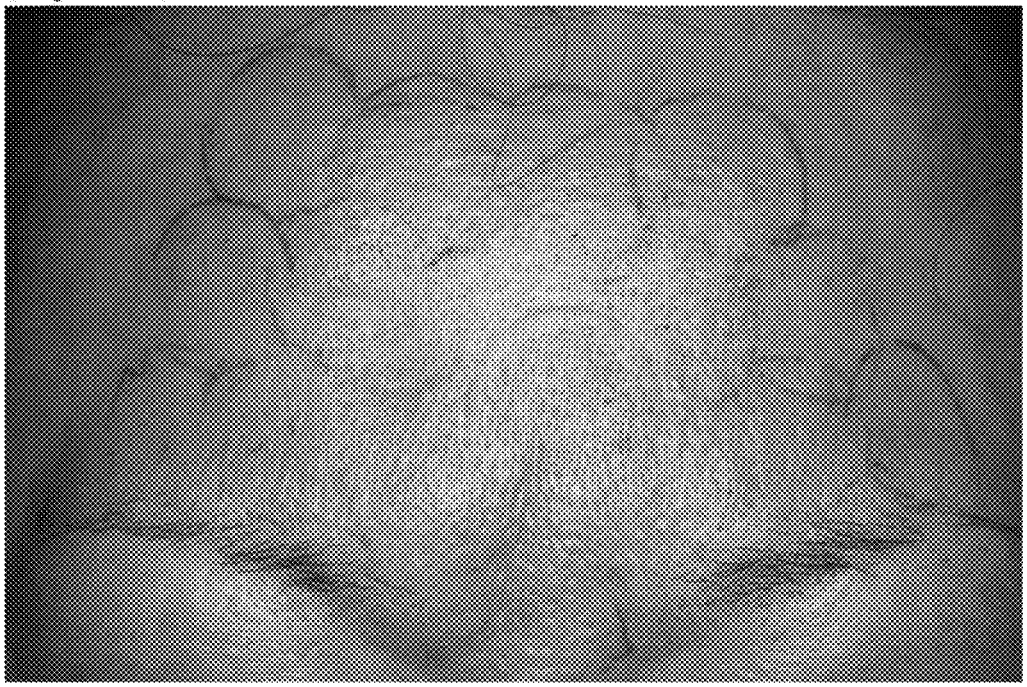
[Figure 6C]
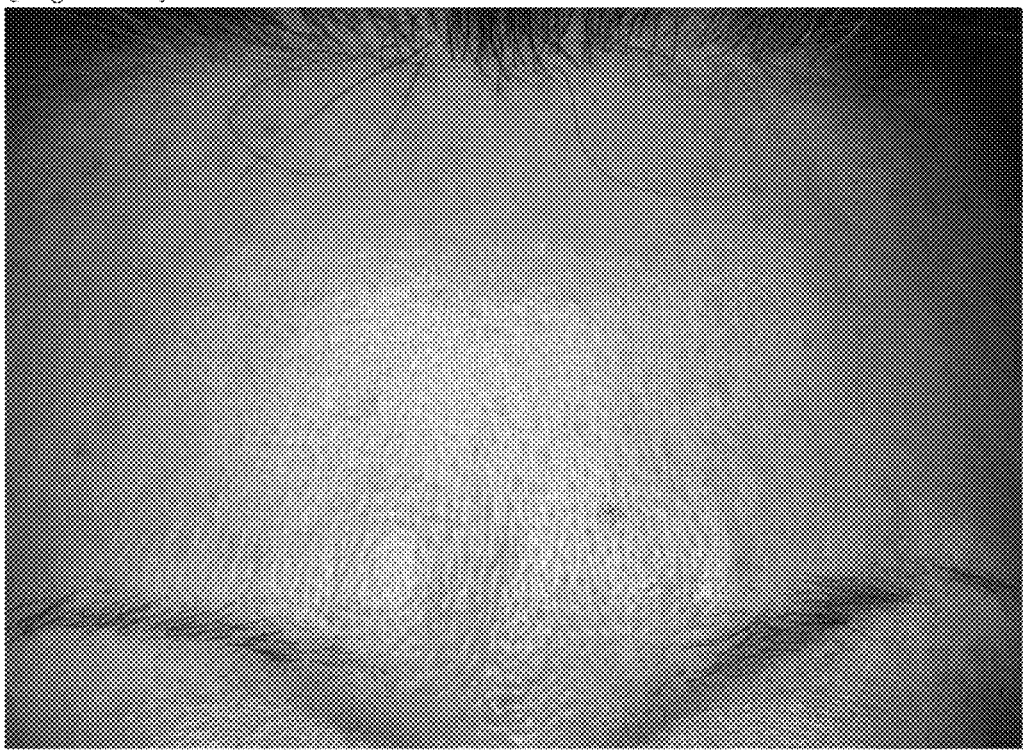

[Figure 7A]
[Figure 7B]
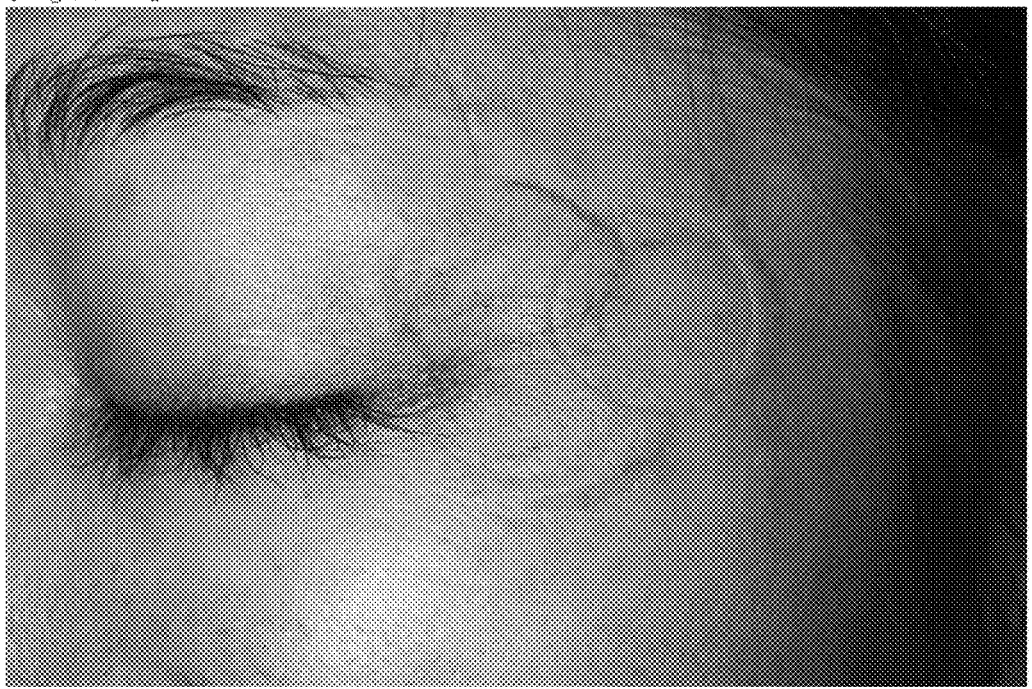

[Figure 7C]

[Figure 8B]

[Figure 8C]

[Figure 9A]

[Figure 9B]

[Figure 9C]

[Figure 10A]

[Figure 10B]

[Figure 10C]

[Figure 11]
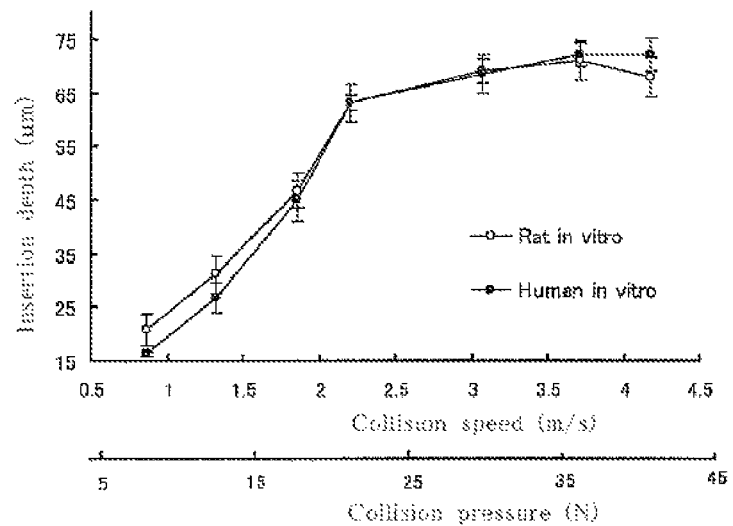
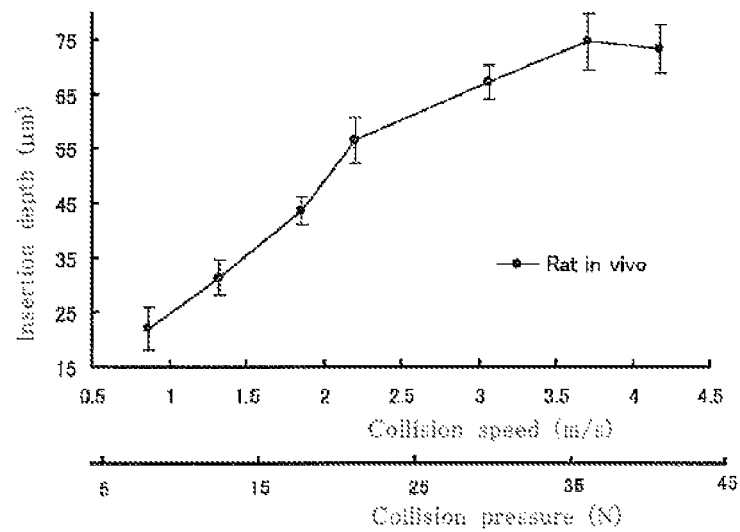

[Figure 12]
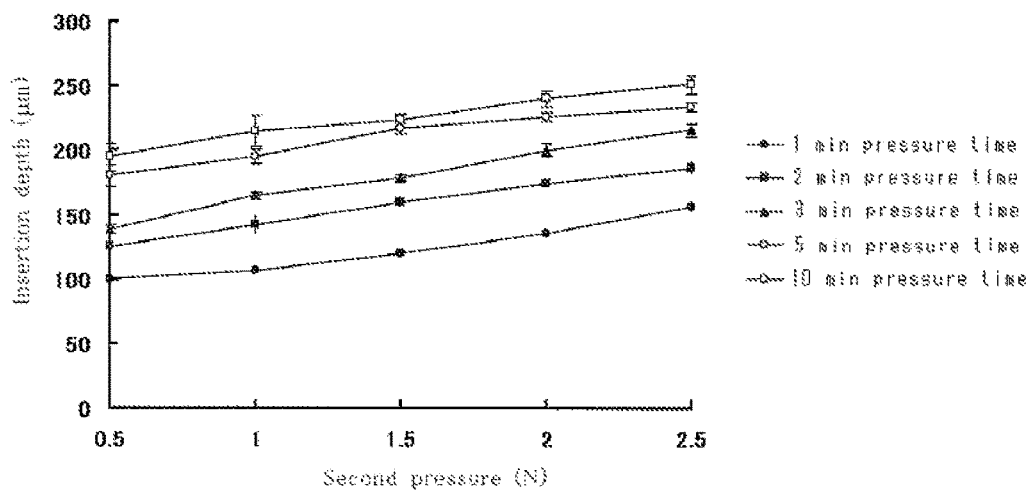
Results of puncturing test for rat skin in vitro
[Figure 13]
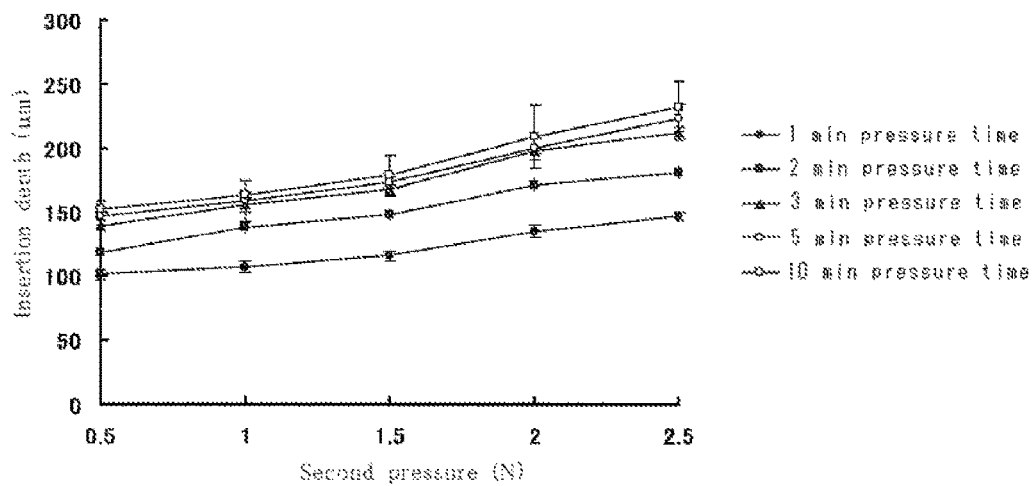
Results of puncturing test for rat skin in vivo

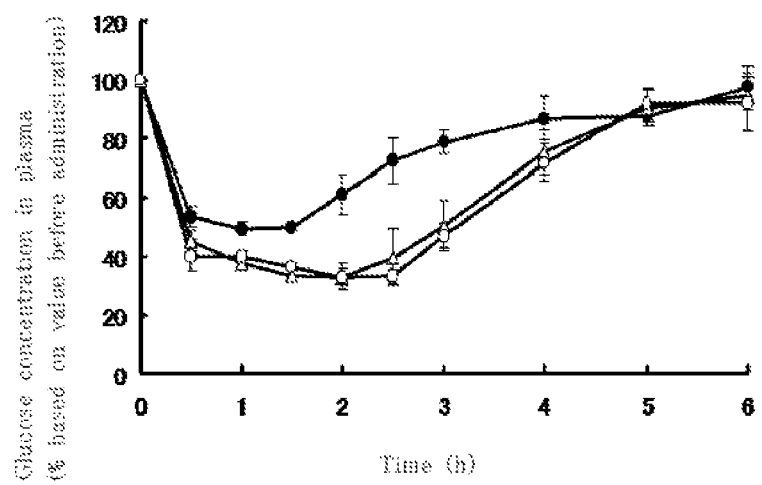
[Figure 14]

MICRONEEDLE ASSEMBLY FORMULATION FOR SKIN TREATMENT

TECHNICAL FIELD

The present invention relates to a microneedle assembly formulation used for prevention or treatment of skin aging, or treatment of skin scar.

BACKGROUND ART

Symptoms of skin aging such as wrinkle, sagging/looseness, pigmentation, depigmentation and thinning of skin and decreasing of skin viscoelasticity have a considerable influence on QOL (Quality of life) of human, particularly women and may become an obstacle on their social lives when the symptoms are severe. Although many symptoms of skin aging were previously believed to develop with advancing age, so-called "physiological aging", in recent years most of the symptoms of skin aging have been considered to be caused by exposure to ultraviolet rays (so-called photoaging). Exposure of skin to ultraviolet rays causes inflammation followed by phenomena such as dermal tissue destruction and deterioration of fibroblast, resulting in the cosmetic change of face and appearance of skin aging.

On the other hand, along with skin aging, skin scarring such as keloids also has a major influence on patient's QOL, and may become an obstacle on his or her social life depending on its affecting level and affected area (such as face). A scar is formed through a healing process of an injury or the like as described below: that is, skin lesion with an injury resulted from a surgical operation or the like onsets wound healing process including hemorrhage/coagulation phase, inflammation phase and proliferation phase, epidermalization is completed after a given period, and then scar-maturing phase at which scar matures leads to wound healing with scar remained.

During this process, scar including hypertrophic scar, scar contracture, keloids and atrophic scar skin may be formed depending on the conditions such as delay of healing, age of a patient and an affected area. Occasionally conditions such as scar contracture, keloids and atrophic scar skin may occur. Although in many cases hypertrophic change calms down over time, in some cases symptoms such as red flare, pruritus and pain are severe to result in significantly deteriorated patient's QOL for an extended period. Additionally, even if scarring settles down, a wide scar and atrophic scar skin are often left, in any case of which patient's QOL may be often deteriorated for a long period.

As stated above, skin aging and skin scarring cause not only patient's cosmetic and functional problems but also social problems including patient's QOL.

Patent Document 1 discloses that local application or topical spraying of basic fibroblast growth factor (bFGF) or platelet derived growth factor (PDGF) etc. enhances regeneration/reconstruction of living tissue of animals and plants and shows an effect/efficacy on a treatment of skin ulcer and bedsore. Furthermore, Patent Documents 2 and 3 disclose that administration of bFGF by dermal or subcutaneous injection enhances skin regeneration and skin wound healing.

However, when an active ingredient is to be administered to an affected area, application or spraying of a liquid preparation containing the active ingredient cannot allow it to remain and penetrate adequately, not to result in sufficient therapeutic effect. An intracutaneous or subcutaneous injection cause a considerable pain to a patient, and has such problems on a clinical application that a physician is required to have a trained skill to evenly inject the injection solution into the dermis and epidermis/dermis junctional region and, in addition, that unevenness of a drug in the tissue at the time of injection becomes evident as uneven level of activity at the time of production of effects. Furthermore, a liquid preparation used for application or subcutaneous injection has poor preservation stability and the ingredient is so susceptible to time degradation that it is difficult to store and handle it.

On the other hand, microneedle type formulations have been studying as a pharmaceutical technology to administer an objective substance transdermally. The microneedles are so tiny that subjects have no pain even when the needles are inserted into the skin. Self-dissoliving microneedles containing an objective substance are inserted through the skin into the body, and the microneedles then dissolve by themselves to result in the objective substance taken into the body.

For example, Patent Document 4 discloses the formation of microneedles using a bio-soluble and thread-forming polymer substance as a base. Patent Document 5 discloses that a microneedle is separated into a part to be inserted into the body and a part to be pushed to improve bioavailability of an objective substance contained in above mentioned microneedle, wherein the objective substance is retained only in the part to be inserted to the body.

In addition, Patent Documents 4 and 5 disclose a microneedle assembly formulation with a plurality of above microneedles formed on a platform such as adhesive skin patch sheet. Patent Document 6 discloses a microneedle assembly formulation with a porous substrate and the production method thereof.

However, the optimal prescription, administration condition and efficiency when a microneedle assembly formulation is used for prevention or treatment of skin aging or treatment of skin scar have not been known yet.

[Patent document 1] Japanese Patent Laid-open Publication No. 2002-249498
[Patent document 2] Japanese Patent Laid-open Publication No. 2003-342194
[Patent document 3] International Publication No. WO 2009/119073
[Patent document 4] International Publication No. WO 2006/080508
[Patent document 5] International Publication No. WO 2009/066763
[Patent document 6] Japanese Patent Laid-open Publication No. 2011-12050

DISCLOSURE OF THE INVENTION

Problems to be Solved by the Invention

The present invention is intended to solve the above mentioned conventional problems and an object thereof is to provide a formulation and a method of administering an active ingredient which allow the active ingredient to be delivered evenly into the site of action in the skin with high efficiency while ensuring stability of the active ingredient over a long time, and which are easily handled and are less painful for patients.

Means for Solving the Problem

The present invention provides a microneedle assembly formulation for skin treatment comprising a platform and a plurality of conical or pyramidal microneedles formed on the platform having a base composed of a bio-soluble and thread-forming polymer substance and an objective substance retained in the base, wherein the objective substance is a substance effective for prevention or treatment of skin aging, or treatment of skin scar.

In one aspect, the microneedles have a first member with a tip part containing the objective substance and a second member with a bottom part not containing the objective substance.

In one embodiment, the first member has an inserting-direction length equal to or shorter than a length of the microneedle inserted into a body at the time of administration of the microneedle assembly formulation for skin treatment.

In one embodiment, the first member has an inserting-direction length equal to or shorter than a length of the microneedle inserted into a dermal layer at the time of administration of the microneedle assembly formulation for skin treatment.

In one embodiment, a substance constituting the base comprises at least one selected from a group consisting of chondroitin sulfate and salts thereof, dextran, hyaluronic acid and salts thereof.

In one embodiment, the objective substance is one selected from a group consisting of various growth factors acting on skin cells and substances promoting production of the growth factors in skin cells.

In one embodiment, the objective substance is basic fibroblast growth factor (bFGF), acidic fibroblast growth factor (aFGF), or a nucleic acid and a plasmid encoding the gene thereof.

In one embodiment, a target symptom for prevention or treatment using the microneedle assembly formulation for skin treatment is skin aging, UV-damaged skin, hypertrophic scar, atrophic scar, keloids, acne scar, hair loss, suture wound, burn wound, ulcer, decubitus, diabetic ulcer or a disease requiring angiogenesis.

In one embodiment, the content of the objective substance is from 0.01 µg to 1.0 mg/patch.

In one embodiment, collision force is applied to insert the microneedles into the skin.

In one embodiment, the collision force is applied at an collision pressure from 5 to 40 N/1.77 $cm^2$.

In one embodiment, collision force is applied to insert the microneedles into the skin, and then secondary pressurization is carried out to insert the microneedles into the skin.

In one embodiment, the secondary pressurization is performed in the range from 0.5 to 2.5 N/1.77 $cm^2$.

Furthermore, the present invention provides a method of administrating a substance effective for prevention or treatment of skin aging, or treatment of skin scar, wherein the method comprises a step of applying a surface on a microneedle-existing side of any of the above mentioned microneedle assembly formulation for skin treatment to an affected area targeted for prevention or treatment of skin aging, or treatment of skin scar, and applying a given pressure to insert the microneedles through the skin into the body.

Effect of the Invention

The present invention allows an active ingredient to be stable over a long time, and thus physicians or patients themselves are allowed to administrate the active ingredient to a site of action easily with high efficiency and evenly to make it possible to enjoy benefit such as alleviation of skin scarring and rejuvenation of skin early in post-treatment.

BRIEF DESCRIPTION OF DRAWINGS

FIG. 1 is a partial perspective view showing a structure of a microneedle assembly formulation for skin treatment according to one embodiment of the present invention.

FIG. 2 is an elevation view showing an example of the microneedle used for the microneedle assembly formulation for skin treatment of the present invention.

FIG. 3 is a photograph showing the course of healing of suture wound in rats with the administration method of the present invention.

FIG. 4 (*a*) is a photograph showing a histopathological image of skin removed from a rat at 4 weeks after the administration and stained with HE staining. FIG. 4 (*b*) is a photograph showing a histopathological image of skin removed from a rat at 4 weeks after the administration and subjected to elastic fiber staining (Elastica van Gieson stain).

FIG. 5 is a graph showing a result of determination of change in width of a scar site in a dermal layer depending on the dosage of the growth factor by measurement on the computer image of the photograph in FIG. 4.

FIG. 6A is a photograph showing the course of healing of transverse wrinkles on the forehead with the administration method of the present invention (57 year-old-female, before treatment).

FIG. 6B is a photograph showing the course of healing of transverse wrinkles on the forehead with the administration method of the present invention (57 year-old-female, immediately after treatment).

FIG. 6C is a photograph showing the course of healing of transverse wrinkles on the forehead part with the administration method of the present invention (57 year-old-female, 3 months after treatment).

FIG. 7A is a photograph showing the course of healing of wrinkles on the left lateral canthus with the administration method of the present invention (50 year-old-female, before treatment).

FIG. 7B is a photograph showing the course of healing of wrinkles on the left lateral canthus with the administration method of the present invention (50 year-old-female, immediately after treatment).

FIG. 7C is a photograph showing the course of healing of wrinkles on the left lateral canthus with the administration method of the present invention (50 year-old-female, 3 months after treatment).

FIG. 8A is a photograph showing the course of healing of wrinkles on the back of the left hand with the administration method of the present invention (61 year-old-female, before treatment).

FIG. 8B is a photograph showing the course of healing of wrinkles on the dorsum of the left hand with the administration method of the present invention (61 year-old-female, immediately after treatment).

FIG. 8C is a photograph showing the course of healing of wrinkles on the dorsum of the left hand with the administration method of the present invention (61 year-old-female, 3 months after treatment).

FIG. 9A is a photograph showing the course of healing of wrinkles on the dorsum of the right hand with the administration method of the present invention (63 year-old-male, before treatment).

FIG. 9B is a photograph showing the course of healing of wrinkles on the dorsum of the right hand with the administration method of the present invention (63 year-old-male, immediately after treatment).

FIG. 9C is a photograph showing the course of healing of wrinkles on the dorsum of the right hand with the administration method of the present invention (63 year-old-male, 3 months after treatment).

FIG. 10A is a photograph showing the course of healing of multiple keloids on the right arm and a keloid on the right cubital region with the administration method of the present invention (24 year-old-female, before treatment).

FIG. 10B is a photograph showing the course of healing of multiple keloids on the right arm and a keloid on the right cubital region with the administration method of the present invention (24 year-old-female, immediately after treatment).

FIG. 10C is a photograph showing the course of healing of multiple keloids on the right arm and a keloid on the right cubital region with the administration method of the present invention (24 year-old-female, 2 months after treatment).

FIG. 11 is a graph showing the relationship between the colligion speed or the collision force and the insertion depth when the collision force is applied to insert the microneedle into the skin.

FIG. 12 is a graph showing the relationship between the applied collision force or the pressure at secondary pressurization and the insertion depth when the collision force is applied to insert the microneedle into the skin and then additional secondary pressurization is carried out to insert the microneedle into the skin in vitro.

FIG. 13 is a graph showing the relationship between the applied collision force or the pressure at secondary pressurization and the insertion depth when the collision force is applied to insert the microneedle into the skin and then additional secondary pressurization is carried out to insert the microneedle into the skin in vivo.

FIG. 14 is a graph showing the time course of the hypoglycemic rate after administration of the microneedle assembly formulation in which insulin, a kind of growth factor, is locally contained in the tip part or administration of an insulin solution to rats.

EMBODIMENT FOR CARRYING OUT THE INVENTION

FIG. 1 is a partial perspective view showing a structure of a microneedle assembly formulation for skin treatment according to one embodiment of the present invention. The microneedle assembly formulation for skin treatment has a platform 1 and a plurality of conical microneedles 2 formed on the platform.

The platform 1 is composed of a material capable of tightly fixing the microneedles 2. The platform 1 is water-insoluble. The platform 1 is hard and does not substantially deform under a room temperature environment. In addition, the platform 1 is porous and does not prevent dryness of the microneedles during the formation of the microneedles.

A preferable platform is a porous plate of plastics such as polyethylene, polymethyl methacrylate, polyvinyl chloride, a chlorinated polyethylene-styrene resin and the like, and a molded product consisting of a water-insoluble excipient for tablets.

Among them, a preferred platform is a molded product consisting of a water-insoluble excipient for tablets because it has excellent productivity and is suitable for a manufacturing process of pharmaceutical products such as sterilization. The excipient for tablets may be a composition containing a plurality of ingredients. Preferable excipients for tablets include cellulose acetate, crystalline cellulose, cellulose derivatives, chitin and chitin derivatives and the like.

The molded product consisting of the excipient for tablets may be produced as is the case with tablets. For example, the excipient for tablets is loaded into a mortar in a tableting machine and compressed with a mallet at an appropriate tableting pressure. Size of the platform may be properly adjusted by changing a diameter of a mortar, filling amount of an excipient for tablets and the tableting pressure.

Shape of the platform is discoidal for example with a diameter from 5 to 50 mm, preferably from 10 to 35 mm and a thickness from 1 to 10 mm, preferably from 2 to 5 mm. Hardness of the platform made of an excipient for tablets is not restricted as long as the platform does not substantially deform when the microneedle assembly formulation for skin treatment is inserted into the skin and is not broken when the microneedles in the microneedle assembly formulation for skin treatment are inserted into the skin by applying collision force.

In one embodiment, when the collapse strength of the platform is measured by placing the platform which is a discoid tablet on a metal cylinder with an outer diameter of 2.0 cm, an inner diameter of 1.2 cm and a height of 2.0 cm and setting a conical attachment to the end of a digital force gauge (FGP-50, NIDEC-SHIMPO CORPORATION), the collapse strength is 30 to 50 N. A thickness of the sample used in this measurement is 2 mm.

FIG. 2 is an elevation view showing an example of the microneedle used in the microneedle assembly formulation for skin treatment of the present invention. The microneedle has a tip part 3 which has a pointed end so that it can pierce the skin. Furthermore, the microneedle has a bottom part 4 which is large in width and is fixed to the platform. Shape of the microneedle may be generally conical or generally pyramidal.

The microneedle has a bottom diameter from 30 to 1000 μm, preferably from 150 to 500 μm and more preferably from 200 to 350 μm and an inserting-direction length from 50 to 1500 μm, preferably from 200 to 750 μm, more preferably from 300 to 550 μm. If the size of the microneedle is outside the range mentioned above, the microneedle may have an insufficient strength and reduced insertability. More specifically, the microneedle has a conical shape with an inserting-direction length of 500 μm and a bottom diameter of 300 μm.

In addition, the microneedles exist on the platform in a density from 30 to 300, preferably from 60 to 200, more preferably from 80 to 140 needles/cm$^2$. If the density of the microneedles is less than 30 needles/cm$^2$, an administration amount of an objective substance tends to be easily insufficient. However, when the density of the microneedles is more than 200 needles/cm$^2$, resistance increases during insertion of the microneedles to result in shallower insertion depth.

The microneedle has a first member 21 and a second member 22. The first member has the tip part 3 and the second member has the bottom part 4. The first member and the second member form a boundary surface 5. The boundary surface between the first member and the second member is generally parallel or substantially parallel with the bottom part of the microneedle.

The first member of the microneedle contains an objective substance to be administered. The second member of the microneedle does not contain the objective substance. In the present invention, the objective substance to be administered is an effective substance for prevention or treatment of skin aging or treatment of skin scar.

The first member preferably has an inserting-direction length equal to or shorter than a length of the microneedle inserted into the body at the time of administration of the microneedle assembly formulation for skin treatment. If the first member has an inserting-direction length exceeding the length of the microneedle inserted into the body, the objective substance existing in the exceeding part is not administered to the body to result in reduced bioavailability of the objective substance.

Preferably, the first member has an inserting-direction length of 233 µm or less. In a typical embodiment, it is difficult to insert the microneedles to a depth more than 233 µm during administration of the microneedle assembly formulation for skin treatment. For example, the first member may have an inserting-direction length of 190 µm or less, or 160 µm or less. It is not necessary to consider the lower limit of a length of the first portion. For example, in the case of an extremely small amount of a drug to be administered, the first member may even have a length of 10 µm.

The microneedle is typically formed of two separate phases: the first member containing the objective substance and the second member not containing the objective substance as shown in FIG. 2. However, the objective substance-containing phase may be properly altered in consideration of the site of action of the objective substance to be used. For example, when the site of action of the objective substance exists in epidermis, the objective substance is preferably contained in the second member.

The microneedle may have an additional separate layer between the first member and the second member. A plurality of layers may exist between the first member and the second member. When a layer is formed between the first member and the second member, the layer may contain the objective substance or may contain a substance exhibiting different action from the objective substance. Concentration of these substances may be properly adjusted depending on the object.

The microneedle may be formed of a single layer. In such a case, the objective substance may be contained throughout the needle or concentration of the objective substance may be increased or decreased depending on the site of the needle. For example, concentration gradient of the objective substance may be generated such that the concentration is higher in a tip part of the needle and lower in a bottom part of the needle.

The microneedle assembly formulation for skin treatment of the present invention is produced, for example by forming a microneedle using a mold and then fixing the obtained microneedle on a platform. As the mold, a plate-like stuff with holes designed to meet shape and alignment of the microneedles is used. Materials of the plate-like stuff used for the mold include a fluorine resin, a silicon resin, an ABS resin and the like.

First, raw materials for the first member of the microneedle, a base, an objective substance and water, are mixed to prepare a first raw material mixture. A polymer substance which is soluble in the body and has a thread-forming property is used as the base. The use of a bio-soluble polymer improves releasing efficiency of the objective substance in the body. The use of a thread-forming polymer enhances strength of the microneedles to improve insertability into the skin.

The bio-soluble and thread-forming polymer substance used is at least one substance selected from a group consisting of polysaccharides having thread-forming property, protein, polyvinyl alcohol, carboxyvinyl polymer and sodium polyacrylate. One of these polymer substances may be used alone or several thereof may be used in combination.

Preferably, the thread-forming polysaccharide is at least one substance selected from chondroitin sulfate and salts thereof (sodium chondroitin sulfate and the like), dextran, dextran sulfate, hyaluronic acid and salts thereof (sodium hyaluronate and the like), cyclodextrin, hydroxypropyl cellulose, alginic acid, agarose, pullulan, glycogen and derivatives thereof.

Preferably, the thread-forming protein is at least one substance selected from serum albumin, serum a acidic glycoprotein, collagen, low molecular collagen, gelatin and derivatives thereof.

Particularly preferred bio-soluble and thread-forming polymer substances include sodium chondroitin sulfate, dextran, sodium hyaluronate and the like because they have been practically used as pharmaceutical products and ensured in terms of safety.

The objective substance is not restricted as long as it is a substance effective for prevention or treatment of skin aging or treatment of skin scar and can be solubilized or dispersed and retained in the above mentioned polymer substance. The objective substance is one of any growth factors having action on skin cells or any substances promoting production of such a growth factor in skin cells.

Specific examples of such a growth factor include all proteins falling within an FGF subfamily, such as basic fibroblast growth factors (bFGF, FGF2) and acidic fibroblast growth factors (aFGF, FGF1), nucleic acids and plasmids encoding the gene thereof, and the like. Compounds expected to be used in combination with FGF: decapentaplegic (DPP), transforming growth factor (TGF) β, sonic hedge hog (shh), Wingless int (Wnt), bone morphogenetic protein (BMP), epidermal growth factor (EGF), insulin like growth factor (ILGF), platelet derived growth factor (PDGF), vascular endothelial growth factor (VEGF) and hepatocyte growth factor (HGF) are also included.

bFGF (FGF2) which is one of the objective substances is a well-known substance and is commercially available (e.g., bFGF product "trafermin (recombinant): Kaken Pharmaceutical Co., Ltd." and the like). bFGF may be in any form of natural or recombinant bFGF or a precursor protein thereof, a natural or recombinant bFGF protein with substitution/deletion/insertion of one or two or more of their constituent amino acids; a protein encoded by cDNA which can hybridize to cDNA of natural human bFGF under stringent conditions (65° C., 1×SSC, 0.1% SDS, or 0.1×SSC, 0.1% SDS); or a protein which has a homology of 75% or more, preferably 80% or more, more preferably 85% or more, yet preferably 90% or more, yet more preferably 95% or more to cDNA of natural human bFGF; or may be a nucleic acid encoding the gene of each protein (cDNA or cDNA plasmid; in the present invention, hereinafter collectively referred to as "gene".) as long as it is effective in preventing/treating skin aging or treating skin scar in the present invention. The gene can also be used in the form of a single plasmid or in the form of a composite plasmid as an expression vector.

Expression vectors used to enhance gene transduction efficiency in the present invention include any expression vectors such as virus vectors, preferably expression vectors for mammalian cells. A promoter comprised in an expression vector used in the present invention is operably linked to bFGF gene and is functional in mammalian (preferably human) cells. The promoter may be inducible or constitutive and, if necessary, tissue-specific. It is known that a timing of expression varies with the kind of a promoter used, and for example, each of early immediate promoter, early promoter and late promoter initiates expression of the gene under its control at its unique time. Therefore, if bFGF is administered to mammal in the form of gene, timing and duration of expression of the bFGF protein can also be adjusted by properly selecting the kind of a promoter.

In addition to bFGF, all FGF subfamily proteins such as aFGF (FGF1), all nucleic acids and plasmids encoding genes thereof are known to have a similar effect to bFGF. The objective substance may contain, in addition to bFGF and aFGF, other substances having or expected to have a similar therapeutic effect for skin aging and skin together. The substances having or expected to have the above mentioned effects include morphogen (morphogen) such as DPP (decapentaplegic), transforming growth factor β (TGF β), Hh (Hedgehog), shh (Sonic Hedgehog), Wnt (Wingless int), bone morphogenic protein (BMP), Epidermal growth factor (EGF) and insulin-like growth factor (ILGF); platelet derived Growth Factor (PDGF), Vascular Endothelial Growth Factor (VGEF), Hepatocyte Growth Factor (HGF) and the like.

Substances enhancing production of the growth factors in skin cells include, for example, eicosanoids such as prostaglandin, extract substances of cyclic adenosine monophosphate (cyclic AMP) and all equivalent synthetic compounds.

In addition, biocompatible substances such as polymer substances, low molecular substances, chemical substances, physiological active substances, proteins (recombinant or natural), peptides and polysaccharides can be employed as the objective substance. Peptides, proteins, nucleic acids or polysaccharides are preferable. The objective substance may be a cell, drug, vaccine, nutrient or cosmetic ingredient.

Then, the first raw material mixture is loaded onto a mold, to which, applying pressure is applied using an application tool or an application apparatus such as squeegee, if necessary, to fill holes formed on the mold with the mixture. The mold may be centrifugalized using a centrifugal machine and the like in order to ensure the filling.

After removing the excess first raw material mixture, the mixture filled in the holes is dried. The drying step is carried out at temperature of 50° C. or lower, preferably room temperature or lower to prevent change of properties of the objective substance, and the like. After drying, volume of the first raw material mixture decreases.

An inserting-direction length of the first member of the microneedle can be adjusted by utilizing this phenomenon. That is, when the first raw material mixture is prepared, solid content concentration in the first raw material mixture is adjusted to adequate concentration so that the solid component of the first raw material mixture remains to a level corresponding to an objective inserting-direction length of the first member of the microneedle after drying the first raw material mixture in the mold.

For example, when the objective substance is bFGF, the inserting-direction length of the first member is preferably adjusted to a length equal to or shorter than a length of the microneedle inserted into a dermal layer at the administration of the microneedle assembly formulation for skin treatment because the site of action is present in a dermal layer. Thereby, bioavailability of the objective substance is more improved.

In human skin, because an epidermis layer, which is laid on a dermal layer, has a thickness from 100 to 200 μm, an inserting-direction length of the second member of the microneedle is preferably 100 μm or more, more preferably 200 μm or more, yet preferably 220 μm or more. On the other hand, from the viewpoint of securing enough administration amount of the objective substance, the inserting-direction length of the second member of the microneedle is preferably 400 μm or less, more preferably 300 μm or less, yet preferably 250 μm or less. In the process of formation of the first member of the microneedle, the inserting-direction length of the first member of the microneedle may be adjusted so that the inserting-direction length of the second member is optimal.

When the objective substance is bFGF, content of the microneedle assembly formulation for skin treatment per patch is, but not restricted to, typically 0.01 μg to 1.0 mg, preferably 0.05 to 100 μg and more preferably 0.2 to 5.0 μg in the case where the microneedle is built up from a single layer. For example, when the surface area of the microneedle assembly is 1.77 cm$^2$, the range can be 0.2 to 100 μg/1.77 cm$^2$. The range of 0.2 to 100 μg/1.77 cm$^2$ can be converted to 0.11 to 56 μg/cm$^2$. In the case where the microneedle has multiple layers, content of the above mentioned objective substance per patch decreases in proportion to volume percentage occupied by the portion containing the objective substance in the microneedle. The amount of the objective substance mixed in the first raw material mixture is determined so that the administration amount of the objective substance is optimized within the above mentioned range in consideration of volume of the microneedle, volume of the portion containing the objective substance in the microneedle, the number of the microneedles formed per patch and the like.

Then, the raw materials of the second member of the microneedle, a base and water, are mixed to prepare the second raw material mixture. Then, the second raw material mixture is loaded onto the mold filled with the dried first raw material mixture, and filled in the holes formed in the mold by using a application tool or a application apparatus if necessary. Before the second mixture is dried, a platform is placed on the mold so as to contact with the second mixture. The platform is porous, so that, when the platform is contacted with the second mixture, ingredients of the second mixture penetrate into pores inside the platform by anchor effect to thereby result in strong bonding therebetween, and at the same time the platform can absorb and release water contained in the second mixture. The mold may be subjected to centrifugal force by using a centrifugal machine and the like to ensure the filling. Then, the second raw material mixture filled in the holes is dried. The drying step is carried out at temperature of 50° C. or lower, preferably room temperature or lower to prevent change of properties of the objective substance, and the like. Subsequently, the platform is removed from the mold to obtain the microneedle assembly formulation for skin treatment of the present invention.

The obtained microneedle assembly formulation for skin treatment is used to prevent or treat human or animal skin aging or treat skin scar. Symptoms to be prevented or treated in the present invention include, specifically, skin aging such as skin wrinkles, fleck, sagging, rough skin, thinning, reduced skin viscoelasticity UV-damaged skin, (atrophy) scar, keloid, acne scar, hair loss, suture wound, burn wound, ulcer, decubitus, diabetic ulcer, diseases requiring angiogenesis and the like.

In the method of administering an effective substance for prevention or treatment of skin aging or treatment of skin scar of the present invention, first, a surface on a microneedle-side of the microneedle assembly formulation for skin treatment (hereinafter referred to as "front surface") is contacted with an affected area, skin, and then a given pressure is applied to insert the microneedles through the skin into the body. Then, further pressure is applied to the back surface of the microneedle assembly formulation for skin treatment. Furthermore, pressurization is continued to fix the microneedle assembly formulation for skin treatment to the affected area. The fixing time is properly adjusted by taking into consideration administration amount of the objective substance, period for healing symptoms and the like.

Although the frequency of the administration is not restricted and single administration may exert a sufficient effect, administration is preferably carried out more than once continuously at regular time period interval, e.g. once a month, for the purpose of prolonged beneficial effect.

In a preferred method of administration, when the microneedle assembly formulation for skin treatment is applied to an affected area, a given collision force is applied to the skin to insert the microneedles through the skin into the body. Collision force may be applied by striking the front surface of the microneedle assembly formulation to the skin at high speed. The pressure to strike the microneedle assembly formulation to the skin (collision pressure) is 5 to 40 N, preferably 10 to 35 N, more preferably 15 to 30 N. If the collision pressure of the microneedle assembly formulation is less than 15 N, insertion depth of the microneedle becomes shallow. On the other hand, even if the collision pressure of the microneedle assembly formulation is increased to more than 35 N, insertion depth of the microneedle does not increase so much.

The collision pressure is expressed as force per surface area of 1.77 $cm^2$ because it is measured using the microneedle assembly formulation patch formulation with a surface area of 1.77 $cm^2$ to be struck on the skin.

The collision pressure can be adjusted by, for example, increasing or decreasing a speed of striking the microneedle assembly formulation to the skin (collision speed). In one embodiment, the collision speed is from 0.5 to 4 m/second, preferably from 1 to 3.5 m/second, more preferably from 2 to 3 m/second.

The method of striking the microneedle assembly formulation to the skin is not restricted. For example, it is only necessary to fix the surface on the side without the microneedles of the microneedle assembly formulation (hereinafter referred to as "back surface") to the tip of a bar, then put it in a suitable sized-guide tube in which the bar can slide back and forth, and then move the bar at high speed while the front surface of the microneedle assembly formulation is directed toward skin. The bar can be moved using, for example, an elastic body such as spring and gum elastic.

However the microneedle sometimes comes out if it is released immediately after the impingement because skin is rich in elasticity and flexibility and has resilience. Therefore, after insertion of the microneedles into skin with collision force applied, further pressure is applied to the back surface of the microneedle assembly (secondary pressurization). This makes the microneedle inserted deeper. In addition, the inserted microneedle is not pushed back and come out, and thus kept in a body. That is, the whole of the first member of the microneedle remains inserted into a body. As a result, bioavailability of the objective substance is improved.

The pressure at the secondary pressurization is from 0.5 to 2.5N, preferably 1 to 2.5 N, more preferably 1.5 to 2.5 N. If the pressure is less than 0.1 N, the inserted microneedle may be pushed back and the first member of the microneedle may come outside the body. On the other hand, increasing the pressure more than 2.5 N is not preferred because of causing patient burden such as skin pain.

The pressure at the secondary pressurization is expressed as force per surface area of 1.77 $cm^2$ because it is measured using the microneedle assembly formulation patch formulation with a surface area of 1.77 $cm^2$ to be contacted to the skin.

The time of the secondary pressurization is from 15 seconds to 5 minutes, preferably 30 seconds to 3 minutes. If the pressure time is less than 15 seconds, the microneedle is not inserted very deeply. On the other hand, even if the pressure time is longer than 5 minutes, the insertion depth of the microneedle is not increased in proportion to the pressure time and almost reaches a ceiling.

Specific embodiments will be described with reference to Examples below. Of course, the present invention is not intended to be limited thereto.

EXAMPLES

Example 1

Purified water (450 μL) was added to 170 mg of lyophilized bFGF drug formulation "FIBLAST Spray 500" (trade name, Kaken Pharmaceutical Co. Ltd.) and 150 mg of sodium chondroitin sulfate (Maruha Nichiro Foods, Inc.) to prepare a viscous solution. The viscous solution was applied on a female mold having 225 inverted cone pores with a depth of about 500 μm and an opening diameter of about 300 μm, per $cm^2$, and filled in the female mold under pressurized condition. After drying, 225 microneedles were removed and obtained from the female mold.

Example 2

Purified water (450 μL) was added to 170 mg of lyophilized bFGF drug formulation "FIBLAST Spray 500" (trade name, Kaken Pharmaceutical Co., Ltd.) and 150 mg of dextran 70 (trade name, Meito Sangyo. Co., Ltd.) to prepare a viscous solution. The viscous solution was applied on a female mold having 225 inverted cone pores with a depth of about 500 μm and an opening diameter of about 300 μm, per $cm^2$, and filled in the female mold under pressurized condition. After drying, 225 microneedles were removed and obtained from the female mold.

Example 3

The dissolving microneedles containing bFGF prepared in Examples 1 and 2 were incubated over three months at −80° C., 4° C., 23° C. or 40° C. and content of bFGF was measured at one week, one month and three months after start of the experiment. The results are shown as a relative content rate of bFGF in the dissolving microneedles kept in each condition at 4° C., 23° C. or 40° C. to the content rate of the bFGF kept at −80° C. assumed to be 100%. Values shown below are expressed as average±SD (standard deviation).

The content rates of bFGF in the dissolving microneedles of Example 1 under the respective storage temperature conditions after one week were 101.6±4.7% (4° C.), 100.9±8.8% (23° C.) and 103.3±4.7% (40° C.).

The content rates of bFGF in the dissolving microneedles of Example 2 under the respective storage temperature conditions after one week were 100.6±2.7% (4° C.), 99.5±1.1% (23° C.) and 99.5±1.5% (40° C.).

The content rates of bFGF in the dissolving microneedles of Example 1 under the respective storage temperature conditions after one month were 100.7±2.0% (4° C.), 98.7±4.9% (23° C.) and 102.8±2.7% (40° C.).

The content rates of bFGF in the dissolving microneedles of Example 2 under the respective storage temperature conditions after one month were 99.4±2.9% (4° C.), 97.7±4.5% (23° C.) and 97.6±4.9% (40° C.).

The content rates of bFGF in the dissolving microneedles of Example 1 under the respective storage temperature conditions after three months were 98.7±7.1% (4° C.), 99.0±7.0% (23° C.) and 100.7±7.6% (40° C.).

The content rates of bFGF in the dissolving microneedles of Example 2 under the respective storage temperature conditions after three months were 107.6±1.7% (4° C.), 101.2±4.3% (23° C.) and 105.7±6.4% (40° C.).

TABLE 1

|  | Example 1 | | | Example 2 | | |
| --- | --- | --- | --- | --- | --- | --- |
|  | 4° C. | 23° C. | 40° C. | 4° C. | 23° C. | 40° C. |
| One week | 101.6 ± 4.7 | 100.9 ± 8.8 | 103.3 ± 4.7 | 100.6 ± 2.7 | 99.5 ± 1.1 | 99.5 ± 1.5 |
| One month | 100.7 ± 2.0 | 98.7 ± 4.9 | 102.8 ± 2.7 | 99.4 ± 2.9 | 97.7 ± 4.5 | 97.6 ± 4.9 |
| Three months | 98.7 ± 7.1 | 99.0 ± 7.6 | 100.7 ± 7.6 | 107.6 ± 1.7 | 101.2 ± 4.3 | 105.7 ± 6.4 |

The dissolving microneedles containing bFGF of Examples 1 and 2 were also shown to be extremely stable under a wide range of storage conditions.

Example 4

While the charged amount of lyophilized bFGF drug formulation "FIBLAST Spray 500" (trade name, Kaken Pharmaceutical Co., Ltd.) was varied from 50 mg to 1.0 mg, 45 to 30 μL of purified water was added to 5.0 mg of sodium chondroitin sulfate and 10 mg of dextran 40 (trade name, Meito Sangyo. Co., Ltd.) to prepare four types of viscous solutions. Each of the viscous solutions was applied on a female mold having 225 inverted cone pores with a depth of about 500 μm and an opening diameter of about 300 μm, per cm², and filled in the female mold under pressurized condition and dried.

About 0.5 g of a 10:1 mixture of cellulose acetate and hydroxypropyl cellulose was loaded onto a mortar in a single punch tableting machine (Ichihashi Seiki, HAND-TAB100), and a tableting pressure of about 10 kN was applied to form a platform for substrae with a diameter of 1.5 cm and a thickness of about 2.0 mm. A viscous solution prepared by adding 150 μL of purified water to 50 mg of sodium chondroitin sulfate and 100 mg of dextran 40 was applied to the platform for substrae, and put on the female mold and dried under pressure.

After six hours, the platform for substrae was removed from the female mold to obtain a patch formulation having 225 microneedles formed and arranged in an array. The resultant patch formulation was put on a polypropylene ring with an outer diameter of 1.5 cm, an inner diameter of 1.3 cm and a height of 0.5 cm previously inserted into a polypropylene PTP packaging container with a luminal bottom diameter of 1.6 cm and a height of 1.0 cm. After putting an aluminum sheet, the resultant was sealed by pressurization and heating and stored before use. The bFGF contents in the resultant dissolving microneedle assembly patch formulations were about 2.0, 1.0, 0.5 and 0.2 μg, respectively.

Example 5

Male Wistar rats weighting about 330 gram were held on surgery boards under pentobarbital anesthesia and about 3 cm-incision was made using a scalpel on its hair-removed abdominal skin. The incision site was sewed three stitches with medical silk suture No. 3 (Murase Hogoshi Company Ltd.). On the second day after the surgery, the stitches were removed. The rats receiving the surgery were divided into two groups, and for the first group, the bFGF-containing dissolving microneedle assembly patch formulation prepared in Example 4 was administered to the skin on the suture site at one week after the surgery.

The second rat group which did not receive the treatment by administration of the patch formulation was monitored for healing of the suture wound on the skin as the control group. FIG. 3 shows photographs displaying the healing process. Healing of the wound on the suture site in the rats of the control group was not unfavorable while in rats receiving administration of the bFGF-containing dissolving microneedle assembly patch formulation, remarkable healing effect began appearing on the suture wound site at 24 hours after administration and the wound was recovered to the conditions looking similar to the surrounding skin at 96 hours after administration. Furthermore, histopathological analysis of the surgical scar site resulting from the experiment also shows that degree of remaining scar was reduced dose-dependently and the patch formulation exerted the effect over an injection preparation.

FIGS. 4 (a) and 4 (b) show histopathological images of skin excised from the rat at four weeks after administration and subjected to HE staining and elastic fiber stain (Elastica van Gieson stain), respectively. These histopathological images demonstrated that administration of the patch containing 0.2 μg of bFGF reduced the width of the scar to half or less of the width of the control and that administration of the patch containing 1.0 μg or more of bFGF reduced the scar to the imperceptible level.

An image of the sample was input into a computer to measure the width of the scar site in the dermal layer. As a result, the measured values were 1117.7±181.6 μm for the control group, 527.3±146.0 μm for 0.2 μg, 251.5±46.3 μm for 0.5 μg, 139.0±40.5 μm for 1.0 μg and 119.0±13.4 μm for 2.0 μg administered group (FIG. 5).

Statistical examination demonstrated that the width of the scar was significantly reduced in the groups receiving 0.2 μg or more as compared to the control group, and the effect was dose-dependent although the increase rate of the effect was lower in the range of 0.5 μg or more.

Example 6

Purified water (225 μL) was added to 35 mg of lyophilized bFGF drug formulation "FIBLAST Spray 500" (trade name, Kaken Pharmaceutical Co., Ltd.), 22.5 mg of sodium chondroitin sulfate and 45 mg of dextran 40 to prepare a viscous solution. The viscous solution was applied on a female mold having 300 inverted cone pores with a depth of about 500 μm and an opening diameter of about 300 μm, per cm².

The female mold was filled under pressurized condition. After drying, a viscous solution prepared by adding 150 μL of purified water to 100 mg of sodium chondroitin sulfate and 50 mg of dextran was applied on the female mold, and filled the female mold. First, about 0.30 g of a 100:10:5 mixture of cellulose acetate, hydroxypropyl cellulose and iron powder was loaded onto a mortar in a single punch tableting machine. Then, about 0.25 g of a 100:10 mixture of cellulose acetate and hydroxypropyl cellulose was placed thereon and a tableting pressure of about 10 kN was applied to form a bilayer tablet, as a platform for substrae, with a diameter of 1.5 cm and a thickness of about 2.0 mm.

A viscous solution prepared by adding 150 μL, of purified water to 100 mg of sodium chondroitin sulfate and 50 mg of dextran 40 was applied on the platform for substrae, and put on the female mold and dried under pressure. After six hours, the platform for substrae was removed from the female mold to obtain a patch formulation with 300 microneedles formed and arranged in an array. The resultant patch formulation was put on a polypropylene ring with an outer diameter of 1.5 cm, an inner diameter of 1.3 cm and a height of 0.5 cm previously inserted into a polypropylene PTP packaging container with a luminal bottom diameter of 1.6 cm and a height of 1.0 cm. After putting an aluminum sheet, the resultant was sealed by pressurization and heating and stored before use. The bFGF content in the bilayer microneedle assembly patch formulation was measured and was about 0.3 μg.

Example 7

The bFGF-containing dissolving microneedle assembly patch formulation prepared in Example 6 was used for the treatments of the following cases 1 to 5. The symptoms, administration conditions and the results are described.

Case 1

57-year-old female. Sixteen sheets of the bFGF-containing microneedle patch formulations were applied by pressing to right and left sides of her forehead and held for about one minute on the same place before removing, followed by coverage with a hydrocolloid dressing. Since the third day after the treatment, only a UV-cut cream was applied externally to the treated area which was monitored over time. Immediately after the treatment, transverse wrinkles in the treated area became shallower while improvement of the skin texture was also observed, and on the third month after treatment, the skin texture of the forehead was improved and transverse wrinkles on both sides of the forehead and glabellar wrinkles between the eyebrows became shallower (FIGS. 6A, B and C).

Case 2

50-year-old female. Three sheets of the bFGF-containing microneedle patch formulations were applied by pressing to wrinkles at left lateral canthus (so-called crow's footprint) and held for three minutes on the same place before removing, followed by coverage with a hydrocolloid dressing. Since the third day after the treatment, only a UV-cut cream was applied externally to the treated area, which was monitored over time. Immediately after treatment, the wrinkles became shallower while improvement of the skin texture was observed, and on the third month after the treatment, the wrinkles at left lateral canthus (so-called crow's footprint) were almost disappeared, and the bFGF-containing microneedle exerted an extremely high effect for this case (FIGS. 7 A, B and C).

Case 3

61-year-old female. Eight sheets of the bFGF-containing microneedle patch formulations were applied by pressing to the dorsum of the left hand and held for three minutes on the same place before removing, followed by coverage with a hydrocolloid dressing. Erythema appeared immediately after applying the bFGF-containing microneedle formulation and then diminished within four to five days, and since the third day after the treatment, only a UV-cut cream was applied externally to the treated area which was monitored over time. On the first month after the treatment, further seven sheets of the bFGF-containing microneedle formulations were applied to the periphery of the previously treated area. Thereafter, improvement of the skin texture was observed, and on the third month after the treatment, the protruded vein of the hand was flattened, atrophied skin was also recovered in terms of thickness, and the bFGF-containing microneedle formulation exerted an extremely high effect for this case (FIGS. 8A, B and C). Any adverse events such as pigmentation were not observed.

Case 4

63-year-old male. Ten sheets of the bFGF containing-microneedle patch formulations were applied by pressing to the dorsum of the right hand and held for three minutes on the same place before removing, followed by coverage with a hydrocolloid dressing. Erythema appeared immediately after applying the bFGF-containing microneedle formulation and almost diminished within five days in this case, and since the third day after the treatment, only a UV-cut cream was applied externally to the treated area which was monitored over time. Since immediately after the treatment, improvement of the skin texture was observed, and on the third months after the treatment, the protruded vein of the hand was flattened, atrophied skin was also recovered in terms of thickness, and the bFGF-containing microneedle formulation exerted an extremely high effect for this case (FIGS. 9A, B and C). Any adverse events such as pigmentation were not observed also in this case.

Case 5

24-year-old-female. Multiple keloids on the right upper limb. Ten sheets of the bFGF-containing microneedle patch formulations were applied by pressing to the keloids on right cubital region and held for three minutes on the same place before removing, followed by coverage with a hydrocolloid dressing. The subjective symptoms such as itching and pain on that area were reduced immediately after the treatment, and on the third month after the treatment, the keloids were flattened, and the treatment was obviously effective in this case (FIGS. 10 A, B and C).

Reference Example 1

(Puncturing Test by Applying a Striking Force)

A silicon resin-based female mold having 225 inverted cone pores with a depth of about 500 μm and an opening diameter of about 300 μm in a circle with a diameter of 1.5 cm was prepared. A viscous concentrated solution was prepared by adding 300 μL of purified water to 100 mg of sodium chondroitin sulfate. The viscous concentrated solution was applied on the pores on the female mold and inserted into them using a squeegee under a pressure of about 3.0 MPa, and then rotated together with the female mold using a tabletop centrifuge to apply centrifugal force in order to fill the pores with the solution. After drying, the viscous concentrated solution prepared by adding 300 μL of purified water to 100 mg of sodium chondroitin sulfate was applied on the female mold. Cellulose acetate for tablets was loaded onto a mortar in a single punch tableting machine, a circular tablet substrate with a diameter of 1.5 cm and a thickness of about 2.0 mm produced by applying a tableting pressure of about 10 kN was then put thereon, and dried and hardened. Thereafter, the substrate was removed from the female mold to obtain a microneedle assembly formulation to be used for the inserting test without any objective substance contained. The area of the surface on the skin-contacting side (front surface) of the microneedle assembly formulation for the inserting test is 1.77 cm$^2$.

In this test, the microneedles of the resultant microneedle assembly formulation were inserted into the skin of a rat in vitro with striking force applied. A commercially available disposable syringe "Terumo Syringe ss-20ESz" was prepared and the tip of the syringe barrel was opened. Then, the back surface of the microneedle assembly formulation was fixed to a tip of a plunger, and then inserted into the syringe barrel whose tip was open. The front surface of the microneedle assembly formulation was directed toward the skin of rats and the plunger was driven using a rubber to strike the microneedles to the skin of rats. At that time, change in insertion depth of the microneedle was determined with changing collision pressure. The results are shown in FIG. 11.

When the collision pressure was increased from 8.4 N to 21.3 N, the insertion depth increased from 20.8 μm to 63.2 μm. However, even if the collision pressure was further increased to 40.2 N, the effect of increasing the insertion depth did not increase so much.

When the same test was carried out using human skin, there was no significant difference observed between rat and human skin. Furthermore, the microneedle assembly formulation was struck on the hair-removed abdominal rat skin of a rat under pentobarbital anesthesia to measure the insertion depth in vivo, and the same results as those the in vitro inserting test were obtained.

Reference Example 2

(In vitro Secondary Pressurization Test)

A microneedle assembly formulation for the insertion test was produced in the same way as in Reference Example 1 and the microneedles were inserted into rat or human skin in vitro by applying an collision pressure of 21.3 N. Thereafter, pressure was applied to the back surface of the microneedle assembly formulation (secondary pressurization). At that time, change in insertion depth of the microneedle was determined with changing pressure and pressure time. The results are shown in FIG. 12.

The insertion depth increased in proportion to the strength of the secondary pressurization. In addition, when the time of the secondary pressurization was extended from one minute to five minutes, the insertion depth increased. There was no significant difference on insertion depth between rat and human skin.

Reference Example 3

(In vivo Secondary Pressurization Test)

A microneedle assembly formulation for the inserting test was produced in the same way as in Reference Example 1 and the microneedle assembly formulation was struck on the hair-removed abdominal rat skin of a rat by applying an collision pressure of 21.3 N under pentobarbital anesthesia to insert the microneedles into the skin of a rat in vivo. Thereafter, further pressure was subsequently applied to the back surface of the microneedle assembly formulation (secondary pressurization). At that time, change in insertion depth of the microneedle was determined with changing pressure and pressure time. The results are shown in FIG. 13.

As with Reference Example 2, the insertion depth into the skin increased with increase of strength of the secondary pressurization and pressure time to one, two and three minutes. However, even if pressure time was extended to three minutes or more, the insertion depth was not observed to increase further in proportion to the pressure time.

As results of Reference Examples 1 to 3, it was demonstrated that applying of an collision pressure from 21.3 N to 40.2 N to the microneedle assembly formulation to insert it into the skin and then secondary pressurization applied at a pressure of 2.5 N for three minutes allowed a length of 212 μm from the tip of the microneedle to be inserted and the pressurization for 10 minutes allowed a length of 233 μm from the tip of the microneedle to be inserted through the skin into the body.

Therefore, a drug is locally placed at a region within 233 μm from the tip of the microneedle to make it possible to achieve bioavailability of an objective substance to 100%.

Reference example 4

A silicon resin-based female mold having 225 inverted cone pores with a depth of about 500 μm and an opening diameter of about 300 μm in a circle with a diameter of 1.5 cm was prepared. Ten mg of insulin, 0.2 mg of Evans blue and 10 mg of sodium chondroitin sulfate were weighted, and each of 70 and 75 μL of degassed purified water was then added thereto to prepare each of viscous concentrated solutions. Each of the viscous concentrated solution was applied on the pores on the female mold and inserted into them using a squeegee under a pressure of about 3.0 MPa, and then rotated together with the female mold using a tabletop centrifuge to apply centrifugal force in order to fill the pores with the solution. After drying, the viscous concentrated solution prepared by adding 400 μL of purified water to 440 mg of sodium chondroitin sulfate was applied on the female mold. Cellulose acetate for tablets was loaded onto a mortar in a single punch tableting machine, a tablet substrate with a diameter of about 1.5 cm and a thickness of about 2.0 mm produced by applying a tableting pressure of about 10 kN was put thereon, and dried and hardened. Thereafter, the substrate was removed from the female mold to obtain two types of microneedle assembly formulations with microneedles containing insulin as an objective substance.

The microneedles of the two different bilayer microneedle assembly patch formulations prepared were monitored by a video microscope (VH-5500, KEYENCE CORPORATION) and a length of the region stained in blue from the tip of the first member was measured. The lengths of the two different bilayer microneedles were 181.2±4.2 μm and 209.5±3.9 μm, respectively.

The insulin contents in the two drug formulations were 1.58±0.03 and 1.72±0.13 IU, respectively. Their effectiveness was examined by administrating either of them to hair-removed abdominal rat skin and the results are shown in FIG. 4. As the control drug formulation, 1.0 unit of an insulin solution was administered to a rat by subcutaneous injection. FIG. 14 shows the measured results on time course of systemic plasma glucose concentrations in rats. ● represents data with the injection product, ○ and Δ represent data with the two bilayer microneedle assembly patch formulations with filled lengths of in about 180 μm and about 210 μm, respectively. After the microneedle assembly patch formulation and the injection preparation containing insulin were administered to rats, values of antihyperglycemic area were compared each other, and it was demonstrated that their relative physiological availabilities (RPAs) were 98.07±0.8% and 98.08±3.1%, respectively.

DESCRIPTION OF THE REFERENCE

1 Platform
2 Microneedle
21 First member
22 Second member
3 Tip part
4 Bottom part
5 Boundary surface

The invention claimed is:

1. A microneedle assembly formulation for use in prevention or treatment of one or more target symptoms selected from the group consisting of skin aging, UV-damaged skin, hypertrophic scar, atrophic scar, keloids, acne scar, hair loss, suture wound, burn wound, ulcer, bedsore, diabetic ulcer or a disease requiring angiogenesis comprising a platform and a plurality of conical or pyramidal microneedles formed on the platform,
   wherein each of the microneedles contains a base composed of a bio-soluble and thread-forming polymer substance and an objective substance retained in the base;
   wherein each of the microneedles has a first layer forming a tip part containing the objective substance and a second layer forming a bottom part not containing the objective substance;
   wherein the objective substance is present in an amount from 0.11 to 56 µg/cm$^2$ of the microneedle assembly;
   wherein the objective substance is basic fibroblast growth factor (bFGF), acidic fibroblast growth factor (aFGF), or a nucleic acid and a plasmid encoding the gene thereof;
   wherein the first layer has a length such that the tip part containing the objective substance is configured to deliver the objective substance to a dermal layer of skin but not to an epidermal layer of skin, and
   wherein the microneedle assembly formulation is configured to prevent or treat the one or more target symptoms without causing pigmentation in the skin to occur.

2. The microneedle assembly formulation according to claim 1, wherein a substance constituting the base further comprises at least one selected from a group consisting of chondroitin sulfate and salts thereof, dextran, hyaluronic acid and salts thereof.

3. A method of administrating a substance effective for prevention or treatment of one or more target symptoms selected from the group consisting of skin aging, UV-damaged skin, hypertrophic scar, atrophic scar, keloids, acne scar, hair loss, suture wound, burn wound, ulcer, bedsore, diabetic ulcer or a disease requiring angiogenesis, wherein the method comprises a step of applying a surface on a microneedle-existing side of the microneedle assembly formulation for skin treatment according to claim 1 to an affected area targeted for prevention or treatment of the one or more target symptoms, and applying a pressure force of 7 to 40 N to insert the microneedles through the skin into a body, wherein the first layer has a length such that the tip part containing the objective substance is configured to delivers the objective substance to a dermal layer of skin but not to an epidermal layer of skin.

4. The method according to claim 3, further comprising applying secondary pressurization force of 0.5 to 2.5 N to the microneedle assembly that is inserted through the skin into the body.

5. The microneedle assembly formulation according to claim 1, wherein the platform is a porous plate of plastics or a molded product consisting of water-insoluble excipient for tablets.

6. The microneedle assembly formulation according to claim 1, wherein the platform is a bilayer tablet composed of a molded layer made from water-insoluble excipient for tablets and a molded layer made from water-insoluble excipient for tablets and iron powder.

7. The microneedle assembly formulation according to claim 1, wherein the microneedles exist on the platform in a density from 30 to 300 needles/cm$^2$.

8. The microneedle assembly formulation according to claim 1, wherein the first layer has an inserting-direction length of 233 µm or less.

9. A microneedle assembly formulation package comprising a push-through pack packaging container, the microneedle assembly formulation for skin treatment according to claim 1 contained in the push-through pack packaging container and an aluminum sheet put on an opening of the push-through pack packaging container, the push-through pack being sealed by pressurization and heating.

10. The microneedle assembly formulation according to claim 1, wherein the second layer has an inserting-direction length of 220 µm or more and 400 µm or less.

11. The microneedle assembly formulation according to claim 1, wherein the second layer has an inserting-direction length of 267 µm or more and 400 µm or less.

* * * * *